United States Patent
Minamoto et al.

(10) Patent No.: US 9,110,073 B2
(45) Date of Patent: Aug. 18, 2015

(54) LIQUID CHROMATOGRAPH, LIQUID CHROMATOGRAPH COLUMN AND FILTER FOR LIQUID CHROMATOGRAPH COLUMN

(75) Inventors: Norimasa Minamoto, Hitachinaka (JP); Masahito Ito, Hitachinaka (JP); Kisaburo Deguchi, Uchinada (JP); Hiroyuki Tanai, Mito (JP); Kiyotoshi Mori, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 161 days.

(21) Appl. No.: 13/202,722

(22) PCT Filed: Mar. 10, 2010

(86) PCT No.: PCT/JP2010/001675
§ 371 (c)(1), (2), (4) Date: Aug. 22, 2011

(87) PCT Pub. No.: WO2010/113392
PCT Pub. Date: Oct. 7, 2010

(65) Prior Publication Data
US 2011/0303599 A1 Dec. 15, 2011

(30) Foreign Application Priority Data
Mar. 31, 2009 (JP) ................................. 2009-083975

(51) Int. Cl.
*G01N 30/60* (2006.01)

(52) U.S. Cl.
CPC .................................... *G01N 30/603* (2013.01)

(58) Field of Classification Search
CPC ........... C10G 2/342; C10G 31/09; B01J 8/22; G01N 30/603
USPC .............. 210/635, 638, 656, 198.2, 205, 206; 422/70
See application file for complete search history.

(56) References Cited

U.S. PATENT DOCUMENTS 3,578,785 A * 5/1971 Patterson .................... 210/198.2
4,359,323 A * 11/1982 LePage ........................... 436/89
(Continued)

FOREIGN PATENT DOCUMENTS

| JP | 2006-227022 A | 8/2006 |
| JP | 2008-256364 | 10/2008 |

OTHER PUBLICATIONS

PTO Translation No. 12-4468 of Japan Patent No. 2008-256364 Jun. 2012.*
(Continued)

*Primary Examiner* — Ernest G Therkorn
(74) *Attorney, Agent, or Firm* — McDermott Will & Emery LLP

(57) ABSTRACT

In a liquid chromatograph, the disulfide adsorption of iron atoms in a filter for a column is avoided and thus peak tailing in a chromatogram is prevented to thereby prevent a lowering in the sample recovery rate. A liquid chromatograph column comprising a hollow tubular column body, a bead-shaped packing material which is packed in the hollow part of the column body, a filter provided with a mesh which has a mesh size smaller than the particle diameter of the packing material, and a cap which presses the filter against the packing material to thereby enclose the packing material within the column body, characterized in that the main component of the filter is nickel or hastelloy.

4 Claims, 2 Drawing Sheets

(56) References Cited

U.S. PATENT DOCUMENTS

| | | | | |
|---|---|---|---|---|
| 4,399,032 A * | 8/1983 | Mott | ............ | 210/198.2 |
| 4,448,691 A * | 5/1984 | Davis | ............ | 210/656 |
| 4,469,597 A * | 9/1984 | Mott | ............ | 210/198.2 |
| 4,565,632 A * | 1/1986 | Hatch et al. | ............ | 210/656 |
| 4,636,316 A * | 1/1987 | Harris et al. | ............ | 210/656 |
| 4,719,011 A * | 1/1988 | Shalon et al. | ............ | 210/198.2 |
| 4,879,039 A * | 11/1989 | Takahashi et al. | ............ | 210/635 |
| 4,888,112 A * | 12/1989 | Kronwald | ............ | 210/198.2 |
| 4,966,695 A * | 10/1990 | Joshua | ............ | 210/198.2 |
| 5,223,435 A * | 6/1993 | Kohr | ............ | 436/89 |
| 5,236,847 A * | 8/1993 | Satake et al. | ............ | 436/89 |
| 5,423,982 A * | 6/1995 | Jungbauer et al. | ............ | 210/198.2 |
| 5,827,426 A * | 10/1998 | Fujii et al. | ............ | 210/198.2 |
| 6,355,165 B1 * | 3/2002 | Sutton et al. | ............ | 210/198.2 |
| 6,440,725 B1 | 8/2002 | Pourahmadi et al. | | |
| 6,518,459 B2 * | 2/2003 | Bennett | ............ | 568/21 |

OTHER PUBLICATIONS

Wikipedia definition of Hastelloy undated.*

E.S. Forbes et al., "Liquid Phase Adsorption/Reaction Studies of Organo-Sulfur Compounds and Their Load-Carrying Mechanism," Asle Transactions, vol. 16, No. 1, Jan. 1973, pp. 50-60.

German Office Action, w/ English translation thereof, issued in German Patent Application No. 11 2010 001 428.0 dated Jan. 4, 2013.

English translation of Chinese Office Action issued in Chinese Patent Application No. CN 2010800086271 dated Jul. 17, 2014.

S. Yagi et al., "Adsorption behavior of sulfer-containing amino acid molecule on transition metal surface studied by S K-edge NEXAFS," Nuclear Instruments and Methods in Physics Research B 199 (2003) 244-248.

* cited by examiner

LIQUID CHROMATOGRAPH, LIQUID CHROMATOGRAPH COLUMN AND FILTER FOR LIQUID CHROMATOGRAPH COLUMN

RELATED APPLICATIONS

This application is the U.S. National Phase under 35 U.S.C. §371 of International Application No. PCT/JP2010/001675, filed on Mar. 10, 2010, which in turn claims the benefit of Japanese Application No. 2009-083975, filed on Mar. 31, 2009, the disclosures of which Applications are incorporated by reference herein.

TECHNICAL FIELD

The present invention relates to a liquid chromatograph, a liquid chromatograph column and a filter for a liquid chromatograph column.

BACKGROUND ART

A liquid chromatograph uses a separation column for separating a sample to be analyzed, and a reaction column for mixing a reagent with the sample to cause reaction in the case of amino acid analysis. When a packing material to be packed in the column has a bead-shape, filters are provided at both ends of the column for the purpose of enclosing the packing material within the column. A mesh size of the filter is set to be smaller than a particle diameter of the packing material in the form of a bead.

As a material of the filter, there has been conventionally used stainless steel including iron Fe as a main component, and chrome Cr, manganese Mn, nickel Ni and molybdenum Mo. Depending on the kind of the stainless steel, niobium Nb, and aluminum Al may be included in addition to chrome Cr, manganese Mn, nickel Ni and molybdenum Mo. The stainless steel includes nickel Ni of about 10 to 14%, and iron Fe of about 70% as the main component.

Amino acids, amino acid analogues and proteins composed by those amino acids have a property of adsorbing on a surface of a stainless steel material. Therefore, when analyzing chemical species such as amino acids and proteins by a liquid chromatograph apparatus using a stainless steel material for a flow channel, the chemical species adsorbs on the surface of the flow channel, and therefore may cause an adverse effect on analysis results.

In particular, it is known that peptides and proteins including cystine which is a kind of amino acid show a strong interaction with iron ions. According to Non Patent Literature 1, disulfide having two sulfur atoms specifically adsorbs on an iron atom on a metallic surface, and temporarily forms iron mercaptide. Ultimately, C—S bond is cut, and the surface of the stainless steel material is covered in a state of iron sulfide. This phenomenon is called a disulfide adsorption phenomenon.

Further, in the case that the filter used for the column of the liquid chromatograph is made from a stainless steel material, a peptide containing cystine adsorbs on a surface of the stainless steel material, and therefore may cause a tailing phenomenon in which a peak obtained in a chromatogram which is an analysis result splays out.

Furthermore, in the case that adsorption of a peptide onto the filter is extreme, most of the peptide is not eluted from the column, which causes the problem that a sample recovery rate is lowered.

CITATION LIST

Non Patent Literature

Non Patent Literature 1: E. S. Forbes, et al: ASLE Trans., 16 (1973) 50

SUMMARY OF INVENTION

Technical Problem

An object of the invention is to avoid a disulfide adsorption phenomenon by iron atoms in a filter of a column in a liquid chromatograph, and thereby prevent a peak tailing phenomenon in a chromatogram to prevent a sample recovery rate from being lowered.

Solution to Problem

In order to solve the above problem, an embodiment of the present invention is characterized in that a separation column or a reaction column of a liquid chromatograph includes a hollow tubular column body, a packing material in the form of beads packed in a hollow part of the column body, a filter with a mesh of a size smaller than a particle diameter of the packing material, and a cap for pressing the filter against the packing material to enclose the packing material within the column body, wherein a main component of the filter is nickel or Hastelloy.

Advantageous Effects of Invention

According to the invention, in a liquid chromatograph, it is possible to avoid a disulfide adsorption phenomenon by iron atoms in a column to prevent amino acids, amino acid analogues and proteins composed of the amino acids from adsorbing on a flow channel, and prevent a peak tailing phenomenon in a chromatogram to prevent reduction of a sample recovery rate.

DESCRIPTION OF EMBODIMENT

An embodiment according to the present invention will be described with reference to the drawings.

Embodiment

Outline of Apparatus

Figure 1:
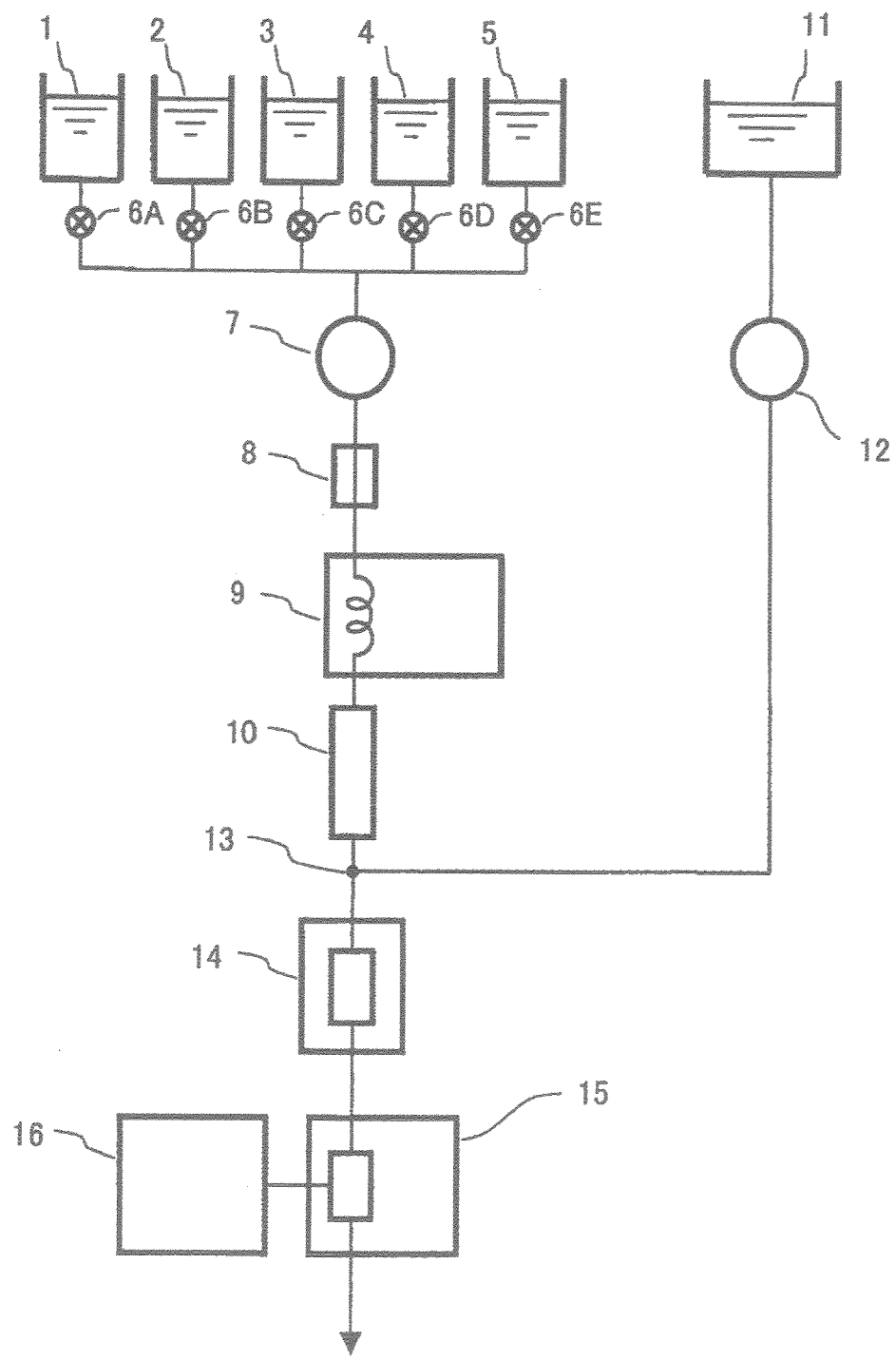
FIG. 1 is a configuration diagram showing a schematic configuration of a liquid chromatograph.

FIG. 1 is a configuration diagram showing a schematic configuration of a liquid chromatograph. In general, when a liquid chromatograph is used for analysis of amino acids, it is called an amino acid analyzer. Line segments which connect respective component devices express flow channels such as piping and the like. A first buffer solution which transports a sample to be analyzed is stored in a vessel 1, a second buffer solution is stored in a vessel 2, a third buffer solution is stored in a vessel 3, and a fourth buffer solution is stored in a vessel 4. Further, a column regenerant solution for cleaning and regenerating a separation column is stored in a vessel 5. A control device not illustrated controls opening and closing of electromagnetic valves 6A, 6B, 6C, 6D and 6E, so that a selected buffer solution is delivered by a buffer solution pump 7 to a flow channel. The buffer solution passes through an ammonia filter 8 which removes ammonia in the buffer solution, and a sample to be analyzed is injected to the buffer solution in an automated sampler 9, and then it reaches a separation column 10. In the separation column 10, the sample to be analyzed, e.g., an amino acid is separated and sent to a mixer 13. Meanwhile, a ninhydrin reagent is stored in a vessel 11, and is fed to the mixer 13 by a ninhydrin reagent pump 12. The separated amino acid and the ninhydrin reagent are mixed in the mixer 13, and are heated in a reaction column 14 to react with each other. Ruhemann's purple of the amino acid that develops by the reaction is detected in a detector 15, and data is sent to a data processing device 16. In the data processing device 16, a chromatogram is created, and screen display and data storage are performed.

(Filter of Separation Column)

Figure 2:
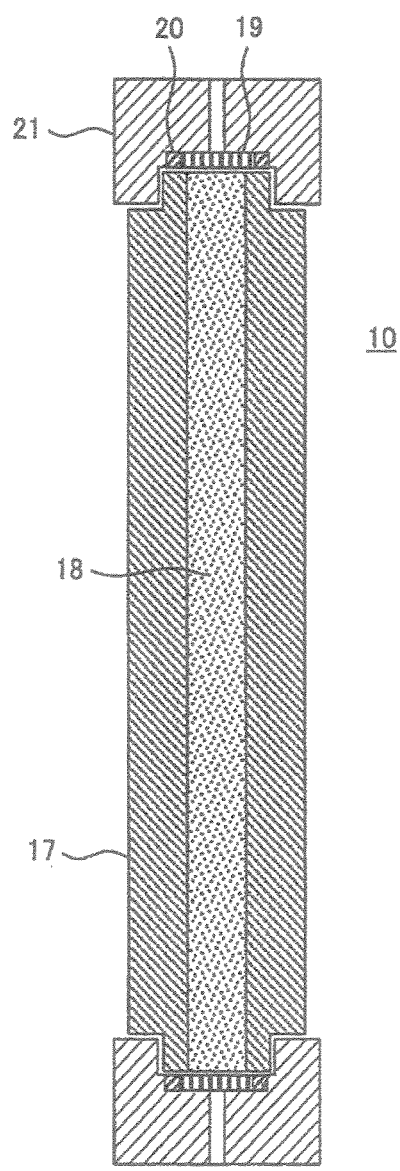
FIG. 2 is a vertical sectional view showing a configuration of a separation column.

FIG. 2 is a vertical sectional view showing a configuration of the separation column. In the separation column 10, a packing material 18 is packed inside a tubular column body 17, and both end portions thereof are enclosed with column filters 19. Further, a periphery of the column filter 19 is pressed with a gasket (packing) 20 to prevent leakage, while a fitting cap 21 is screwed onto the column body 17, for example, to press the column filters 19 against the packing material 18 to enclose it.

TABLE 1

| | Fe (WEIGHT %) | Ni (WEIGHT %) | 30% HYDROCHLORIC ACID (24° C.) |
|---|---|---|---|
| HASTELLOY | 1–18 | 43–71 | ⊚ |
| SUS316 | 68 | 12 | X |
| TITANIUM | ≈0 | ≈0 | ◯ |

⊚: CORROSION RATE: <0.127 mm/year
◯: CORROSION RATE: 0.127–1.27 mm/year
X: CORROSION RATE: >1.27 mm/year Table 1 is a list showing content amounts of iron and nickel, and corrosion rates with respect to Hastelloy, stainless steel and titanium. As for the corrosion rate, Hastelloy has the lowest corrosion rate when 30% of hydrochloric acid solution is continuously sprayed under the environment at 24 degrees centigrade, and therefore, it is found out that Hastelloy is excellent in corrosion resistance. In the embodiment of the present invention, a nickel alloy is adopted as a material of the column filter 19, and especially, Hastelloy is used. As for the specifications of the filter part of the column filter 19, there is used the one with nominal filtration precision of 0.5 micrometers with respect to the particle diameter of three micrometers of an ion exchange resin which is the packing material. Further, the outside diameter of the column filter 19 is 4.6 millimeters, and the thickness thereof is 1.6 millimeters.

A main component of Hastelloy is nickel while Hastelloy contains only 1 to 18 weight % of iron, and therefore, a disulfide adsorption phenomenon is hardly caused. Accordingly, when an amino acid is a sample to be analyzed, adsorption of disulfide molecule cystine, which is a kind of amino acid, onto the column filter 19 can be avoided, and therefore, a peak tailing phenomenon in an obtained chromatogram can be restrained. Similarly, homocystine, cysteine homocysteine disulfide and the like which are disulfide molecules also can restrain the peak tailing phenomenon in a chromatogram.

Further, if peptides adsorbs on the filter part of the column filter 19, the peptides block a flow so that most of the sample may not be eluted from the separation column 10, and thereby analysis cannot be performed. According to the present embodiment, the amino acid components do not adsorbs on the column filter 19, and therefore, reduction in an amino acid sample recovery rate can be prevented.

As for the recovery rate in the case that peptides and proteins having disulfide amino acids as composing molecules are adopted as a sample to be analyzed, it is 50% when using stainless steel for the column filter, and is 100% when using Hastelloy for the column filter, according to experiments by the applicants.

Further, acid resistance and corrosion resistance are required for the column filter 19. For example, in the case of a 40 components amino acid biological fluid analysis method, several tens millimoles/L of lithium citrate buffer solution with an acidity of pH 2.8 is delivered as a buffer solution. Hastelloy is an acid resistant metal, and can be used for a sample solution with an acidity up to pH 2. Further, as is understood from Table 1 shown above, Hastelloy is excellent in corrosion resistance as compared with stainless steel and titanium.

(Filter of Reaction Column)

In an amino acid analyzer, after an amino acid component is separated in the separation column 10, the amino acid component is mixed with a ninhydrin reaction reagent, and is heated to 135 degrees centigrade in the reaction column 14, whereby Ruhemann's purple is generated, and the absorbance of visible light of 570 nanometers is detected by the detector 15. As an device which performs the mixing and color development reaction, a columnar reactor is used in the reaction column 14. The structure of the reaction column 14 is similar to that of the separation column 10 shown in FIG. 2, and a column body has an inside diameter of three to six millimeters, and a length of 40 to 80 millimeters. Inside of this, spherical or granular ceramics beads with a particle diameter of about 100 micrometers that is inert in chemical reaction, or the like are packed as a packing material. For the purpose of preventing discharge of the beads from the reaction column 14, filters are provided at both end portions.

Amino acids having passed through the separation column 10 are fed to the reaction column 14, however, if a disulfide adsorption phenomenon occurs in the filter of the reaction column 14, a peak tailing phenomenon in a chromatogram and reduction in a sample recovery rate occur. Accordingly, Hastelloy is also used for the filter of the reaction column 14. For the purpose of enclosing the bead particles with particle diameters of 50 to 100 micrometers, 1 to 30 micrometers is selected for the filter parts. The outside diameter is 3 to 6 millimeters, and the thickness is 0.5 to 2.5 millimeters.

The ninhydrin reaction reagent fed to the reaction column 14 from the mixer 13 shown in FIG. 1 is a several moles/L of lithium citrate buffer solution with an acidity of about pH 6, and therefore, it is conceivable that the filter used for the reaction column 14 does not need to have acid resistance. However, if a ninhydrin reaction reagent is not delivered while the ninhydrin reaction reagent is to be mixed with the buffer solution in the mixer 13, a several millimoles/L of lithium citrate buffer solution with an acidity of pH 2.8 will be delivered under a high temperature of about 135 degrees centigrade. Therefore, the filter of the reaction column 14 also needs to have acid resistance.

When a buffer solution with an acidity of pH 2.8 is delivered to the filter made from stainless steel under the environment at 135 degrees centigrade, corrosion is found in observation after a lapse of 24 hours. In contrast with this, when the buffer solution is delivered to the filter made from Hastelloy under the same conditions, no corrosion is found.

As described above, according to the present invention, since it is possible, in a liquid chromatograph, to avoid a disulfide adsorption phenomenon by iron atoms in the filters of the columns, and prevent amino acids, amino acid analogues and proteins composed of the amino acids from adsorbing on the flow channel, a peak tailing phenomenon in the chromatogram is prevented and reduction in sample recovery rate can be prevented. A more stable result can be obtained at each analysis, and accuracy and repeatability of quantitative analysis are enhanced.

REFERENCE SIGNS LIST 1, 2, 3, 4, 5, 11: VESSEL
6A, 6B, 6C, 6D, 6E: ELECTROMAGNETIC VALVE
7: BUFFER SOLUTION PUMP
8: AMMONIA FILTER
9: AUTOMATED SAMPLER
10: SEPARATION COLUMN
12: NINHYDRIN REAGENT PUMP
13: MIXER
14: REACTION COLUMN
15: DETECTOR
16: DATA PROCESSING DEVICE
17: COLUMN BODY
18: PACKING MATERIAL
19: COLUMN FILTER
20: GASKET
21: FITTING CAP

The invention claimed is:

1. A reaction column used for a liquid chromatograph, the liquid chromatograph comprising:
a first pump for delivering a mobile phase,
a sample injection port for injecting a liquid sample into a flow channel of the mobile phase delivered from the first pump, wherein the liquid sample comprises at least one component selected from the group consisting of cystine, cystein homocystine and homocystein;
a separation column for separating sample components; and
a second pump arranged downstream from the separation column for delivering a reaction reagent to be mixed with the sample components exiting the separation column,
wherein the reaction column is located downstream from a junction where the reaction reagent and the sample components exiting the separation column are mixed, and wherein the reaction column comprises:
a hollow tubular column body;
a packing material in the form of beads packed in a hollow part of the column body;
a filter with a mesh of a size smaller than a particle diameter of the packing material; and
a cap for pressing the filter against the packing material to enclose the packing material within the column body, wherein:
a main component of the filter is nickel, and wherein the reaction column is heated to facilitate a reaction between the reaction reagent and the sample components resulting in a chemical modification of said at least one component selected from the group consisting of cystine, cystein homocystine and homocystein.

2. The reaction column according to claim 1, wherein a nickel content amount of the filter is 40% or more, and an iron content amount thereof is 20% or less.

3. The reaction column according to claim 1, wherein a nickel content of 43 to 71 wt % and an iron content of 1 to 18 wt %.

4. The reaction column according to claim 1, wherein the reaction reagent is a ninhydrin reagent.

* * * * *